United States Patent [19]

Mitschke et al.

[11] 4,265,831
[45] May 5, 1981

[54] PROCESS FOR THE PREPARATION OF HYDROXYALKYLPERFLUOROALKANE SULPHONAMIDES

[75] Inventors: Karl-Heinz Mitschke, Odenthal; Klaus Geisler, Bonn-Beuel; Hans Niederprüm, Monheim, all of Fed. Rep. of Germany

[73] Assignee: Bayer Aktiengesellschaft, Leverkusen, Fed. Rep. of Germany

[21] Appl. No.: 54,338

[22] Filed: Jul. 2, 1979

[30] Foreign Application Priority Data

Jul. 22, 1978 [DE] Fed. Rep. of Germany ....... 2832346

[51] Int. Cl.$^3$ ........................................... C07C 143/74
[52] U.S. Cl. ......................................... 564/96; 564/97
[58] Field of Search ..................................... 260/556 F

[56] References Cited

U.S. PATENT DOCUMENTS

| 2,915,554 | 12/1959 | Ahlbrecht et al. | 260/556 F |
| 4,079,084 | 3/1978 | Houghton | 260/556 F X |
| 4,175,096 | 11/1979 | Reitz et al. | 260/556 F |

FOREIGN PATENT DOCUMENTS

| 619959 | 5/1961 | Canada | 260/556 F |
| 2307377 | 8/1974 | Fed. Rep. of Germany | 260/556 F |
| 2639473 | 3/1978 | Fed. Rep. of Germany | 260/556 F |

Primary Examiner—Thomas A. Waltz
Attorney, Agent, or Firm—Sprung, Felfe, Horn, Lynch & Kramer

[57] ABSTRACT

A process for the preparation of a hydroxyalkylperfluoroalkane sulphonamide of the formula

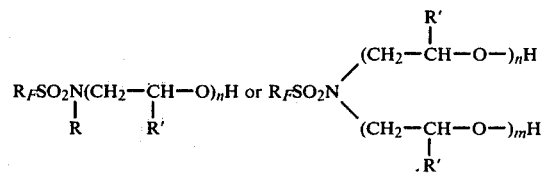

wherein
  $R_F$ is a perfluoroalkyl group having from 1 to 20 carbon atoms;
  R and R' each independently is hydrogen or an alkyl, hydroxyalkyl, haloalkyl, cycloalkyl, aralkyl, alkenyl or aryl radical; and
  m and n each independently is an integer from 1 to about 30,
comprising reacting a perfluoroalkylsulphonamide of the formula

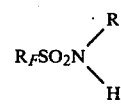

with an epoxide of the formula

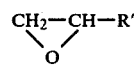

in the presence of a basic catalyst.

4 Claims, No Drawings

PROCESS FOR THE PREPARATION OF HYDROXYALKYLPERFLUOROALKANE SULPHONAMIDES

This invention relates to a new process for the preparation of hydroxyalkyl-perfluoroalkane sulphonamides corresponding to one of the following general formulae:

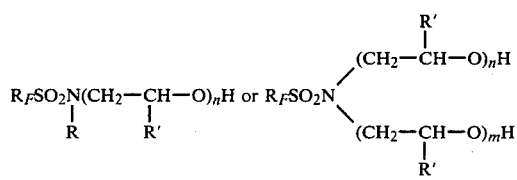

wherein $R_F$ represents a straight- or branched-chain perfluoroalkyl group having from 1 to 20 carbon atoms, preferably from 1 to 10 carbon atoms;

R and R' each independently represents hydrogen or an alkyl, hydroxyalkyl, haloalkyl, cycloalkyl, aralkyl, alkenyl or aryl group; and n and m independently represent values of from 1 to 30.

Hydroxyalkyl-perfluoroalkane sulphonamides may be used for various purposes, in particular as intermediate products for the production of substances used for the impregnation of textiles, leather, paper or the like to render them oleophobic or hydrophobic or as highly surface active agents. They may also be used as levelling agents for waxes, fats, lacquers, and other substances.

Hydroxyalkyl-perfluoroalkane sulphonamides have hitherto been prepared (see e.g. U.S. Pat. No. 2,803,656) by the reaction of alkali metal salts of perfluoroalkane sulphonic acid amides with halogen hydrins.

This method is, however, very involved since it consists of a two-stage reaction. The sulphon-amides in alcoholic solution are first reacted with an alkali metal hydroxide to form the corresponding salt. The reaction proper with the chloroalkanol or bromoalkanol is then carried out after removal of the solvent by distillation. Moreover, the reactions take place in a heterogeneous reaction system and therefore require long reaction times (of the order of more than 10 hours) during which considerable decomposition reactions take place so that a complicated procedure of purification is required and the yields are reduced.

The obvious reaction for the preparation of perfluoroalkyl-sulphonamidoalkanols, namely, the reaction of perfluoroalkyl-sulphonyl fluoride with, for example, N-alkylethanolamine, cannot be carried out since both the NH-group and the OH-group react with the sulphonylhalide, and the ester formed in the reaction undergoes numerous secondary reactions due to its powerful alkylating properties. Blocking the hydroxyl function, e.g. by silylation, is no answer to the problem since the trimethylsilyl group undergoes a very rapid exchange reaction with sulphonyl fluoride to form trimethylfluorosilane and higher alkylated nitrogen compounds (see Ann. 731, 58 (1970)).

Although the process according to German Offenlegungsschrift No. 2,307,377 is based on the reaction of perfluoroalkylsulphonamides with epoxides tertiary amines are the only catalysts suitable for this process. Alkali metal hydroxides and alcoholates and other catalysts fail to produce the required result. Moreover, the process must be carried out in solvents, so that isolation of the reaction products becomes complicated.

It is an object of the present invention to provide a simple and economical process for the preparation of hydroxyalkyl-perfluoroalkane sulphonamides.

The present invention relates to a process for the preparation of hydroxyalkyl-perfluoro-alkanesulphonamides corresponding to one of the following general formulae:

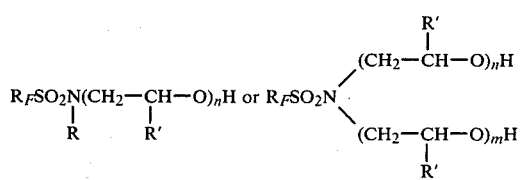

wherein $R_F$ represents a straight- or branched-chain perfluoroalkyl group having from 1 to about 20 carbon atoms, preferably from 1 to about 10 carbon atoms;

R and R' independently represent hydrogen or an alkyl, hydroxylalkyl, haloalkyl, cycloalkyl, aralkyl, alkenyl or aryl group and n and m independently represent values of from 1 to about 30; characterised in that perfluoroalkylsulphonamides corresponding to the following general formula:

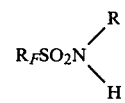

are reacted with epoxides corresponding to the following general formula:

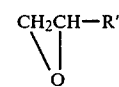

wherein $R_F$, R and R' are as defined above; in the presence of organic or inorganic metal compounds which are basic in reaction and/or basic ion exchange resins and catalysts.

Preferably R and R' are hydrogen, alkyl of up to 6 carbon atoms optionally substituted by hydroxy or halogen, cycloalkyl of 3 to 8 carbon atoms, benzyl, phenethyl, alkynyl of up to 4 carbon atoms, phenyl or naphthyl.

It has surprisingly been found that in contradiction to the teaching given in German Offenlegungsschrift No. 2,307,377, the reaction according to the present invention proceeds smoothly, e.g. with alkali metal hydroxides or alcoholates, and that no solvents are required. Isolation of the end products is therefore greatly facilitated since the products obtained require no purification, e.g. by vacuum distillation. On the commercial scale, this method of purification is extremely complicated in the case of such compounds and a considerable disadvantage since in spite of the low pressures employed, which are less than 1 Torr, sump temperatures of up to 200° C. are still necessary in some cases, and such high temperatures inevitably lead to a high degree of decomposition.

The process according to the present invention is carried out by introducing the epoxides into the solvent free perfluoroalkylsulphonamide with a suitable catalyst. The reactions are carried out at temperatures of about 40° to 170° C., preferably about 60° to 140° C. The reactions are preferably carried out at normal pressure, but excess pressure may be employed (for example, in an autoclave). The process may be carried out either continuously or intermittently.

When basic ion exchange resins are used, these may be removed after the reaction, for example by filtration of the solvent-free melt, and may be used again. When alkali metal hydroxides or similar substances are used, for example, the reaction products may be purified by washing with hot water, optionally under pressure, followed by filtration from the added catalysts and drying in a vacuum, although the catalysts may also be left in the product.

The starting materials used are perfluoroalkylsulphonamides which, as is well known, may be obtained by reaction of the appropriate fluorides with ammonia or primary amines. The sulphonamides may be distilled if desired. If purification by distillation is to be carried out, this is preferably done at this stage rather than at the stage of the end product due to the more advantageous molecular weight.

The following are examples of the perfluoroalkylsulphonamides which may be used:
$CF_3SO_2NH-CH_3$, $CF_3SO_2NH_2$, $C_4F_9SO_2NH_2$, $C_4F_9SO_2NH-CH_3$,
$C_4F_9SO_2NH-C_4H_9$, $C_4F_9SO_2NH-CH_2-CH=CH_2$,
$C_8F_{17}SO_2NH_2$, $C_8F_{17}SO_2NH-CH_3$, $C_8F_{17}SO_2NH-C_5H_{11}$,
$C_8F_{17}SO_2NH-CH_2C_6H_5$.

Any compounds containing epoxide groups may in principle be used as the alkylene oxide, for example the following: ethylene oxide, propylene oxide, glycidol, styrene oxide, butylene oxides, epichlorohydrin, phenoxypropylene oxides or mixtures thereof. Epoxides having from 2 to 4 carbon atoms are particularly suitable.

The catalysts used are organic or inorganic metal compounds which are basic in reaction or basic ion exchange resins.

Suitable inorganic metal compounds which are basic in reaction include, for example, alkali metal oxides, hydroxides, carbonates or phosphates, such as NaOH, KOH, $K_2CO_3$ or $Na_3PO_4$, or alkaline earth metal oxides or hydroxides or alkali metal or alkaline earth metal hydrides, such as NaH.

Suitable organic metal compounds which are basic in reaction include metal alkyls or aryls, such as butyl lithium or phenyl sodium, or secondary metal amides, such as lithium diisopropylamide, or metal alcoholates, such as sodium methylate or potassium tertiary butylate, or metal carboxylates, such as sodium acetate, or the alkali metal salts of the sulphonamides to be used, $R_FSO_2N(R)Na$.

The catalysts are used in quantities of about 0.01 to 20 mol %, preferably about 0.2 to 10 mol %, based on the sulphonamide.

The basic catalysts used may also be ion exchange resins in which the characteristic groups for the ion exchange are quaternary ammonium salts and the carriers may be, for example, polystyrene or phenol/formaldehyde resins. Substances of this type include, for example, the products marketed by BAYER AG under the name of Lewatite ®, which act as strong bases. They are used in quantities of about 0.1 to 20 g per mol of sulphonamide used.

Although a higher proportion of catalyst may be used, this is neither economical nor useful, nor is any purpose achieved by reducing the quantity of catalysts.

The process according the present invention is illustrated by the following examples.

EXAMPLE 1

24.2 g (0.55 mol) of ethylene oxide were added dropwise within 30 minutes at about 120° C. to a solventfree melt of 256.6 g (0.5 mol) of N-methyl-perfluorooctane sulphonamide and 0.5 g (0.0089 mol) of potassium hydroxide in a three-necked flask equipped with stirrer, internal thermometer, dry ice reflux condenser and coolable dropping funnel having an inlet tube connected to its outflow and reaching to the bottom of the flask. The reaction mixture is stirred for about 2.5 hours after the addition of ethylene oxide. After removal of unused ethylene oxide (or epoxides in general) or other volatile compounds in a vacuum, 279 g (~ quantity, including catalyst) of a product corresponding to the following formula:

$C_8F_{17}SO_2N(CH_3)CH_2CH_2OH$ are obtained. The product melts in the range of from 90° to 95° C. and has an OH number of 3.1% (theoretical value 3.05%). Its composition was determined by NMR spectroscopy and gas chromatography.

To remove the catalyst, the product was washed using hot water and the mixture was cooled with stirring. The product, which was obtained in a granular form, was filtered and dried in a vacuum. Melting range 94° to 97° C.

EXAMPLE 2

592 g (~ quantity including catalyst) of the compound $C_8F_{17}SO_2N(CH_2-CH_2-OH)_2$ melting in the range of from 136° to 140° C. and having an OH number of 5.77% (theoretical value 5.79%) was obtained within 4 hours by a method analogous to that of Example 1 from 499 g (1 mol) of perfluorooctane sulphonamide, 2 g (0.036 mol) of potassium hydroxide and 92.5 g (2.1 mol) of ethylene oxide at about 120° C. The product was identified by NMR spectroscopy and gas chromatography.

EXAMPLE 3

1039 g (~ quantity including catalyst) of a product of the formula $C_4F_9SO_2N(CH_2-CH_2-OH)_2$ melting at about 75° C. and having an OH number of 8.78% (theoretical value 8.78%) were obtained within 4 hours by a method analogous to that of Example 1 from 802.5 g (2.68 mol) of perfluorobutane sulphonamide, 2 g (0.036 mol) of potassium hydroxide and 248 g (5.63 mol) of ethylene oxide at from 90° to 100° C. The product was identified by NMR spectroscopy and gas chromatography.

EXAMPLE 4

Using the same experimental arrangement as in Example 1, 156.6 g (0.5 mol) of N-methyl-perfluorobutane sulphonamide and 24.2 g (0.55 mol) of ethylene oxide were reacted for about 2 hours at from 70° to 90° C. in the presence of 10 g of basic ion exchange resin "MP 500" (groups of cross-linked polystyrene carrying hydroxyl ions). After removal of the ion exchange resin by filtration and of excess ethylene oxide by evaporation under vacuum, 178 g (~ quantity) of a product corresponding to the formula $C_4F_9SO_2N(CH_3)CH_2CH_2OH$ were obtained.

EXAMPLE 5

Using the experimental arrangement from Example 1, 94 g (~ quantity including catalyst) of the compound $C_4F_9SO_2N(CH_3)CH_2$—$CH(CH_3)OH$ melting in the range of from 38° to 41° C. were obtained from 78.3 g (0.25 mol) of N-methyl perfluorobutane sulphonamide, 1 g (0.009 mol) of potassium tertiary butylate and 15.3 g (0.263 mol) of propylene oxide by reaction at a temperature of from 100° to 120° C. within about 2.5 hours, followed by removal of excess propylene oxide under vacuum. After washing using hot water as in Example 1, the melting range was from 45° to 48° C.

EXAMPLE 6

94 g (~ quantity including catalyst) of the compound $C_4F_9SO_2N(CH_3)$—$CH_2$—$CH(CH_3)OH$ melting in the range of from 38° to 40° C. were obtained as in Example 1 from 78.3 g (0.25 mol) of N-methyl-perfluorobutane sulphonamide, 1.2 g (0.0087 mol) of potassium carbonate and 15.3 g (0.263 mol) of propylene oxide. The product was identified by NMR spectroscopy and gas chromatography.

After washing using hot water, the melting range was from 45° to 48° C.

EXAMPLE 7

112 g (~ quantity including catalyst) of the compound of the formula $CF_3SO_2N(CH_3)CH_2$—$CH(CH_3)OH$, which was identified by NMR spectroscopy, were obtained analogously to Example 1 from 81.6 g (0.5 mol) of N-methyl-perfluoromethane sulphonamide, 1 g (0.018 mol) of potassium hydroxide and 32.5 g (0.55 mol) of propylene oxide.

EXAMPLE 8

65 g (~ quantity including catalyst) of the compound $C_8F_{17}SO_2N(CH_2$—$CH(OH)$—$CH_2OH)_2$ were similarly obtained from 49.9 g (0.1 mol) of perfluorooctane sulphonamide, to which 10 ml of dimethylformamide had been added, 200 mg (0.0036 mol) of potassium hydroxide and 16.5 g (0.22 mol) of glycidol at from 120° to 130° C. The compound was confirmed by NMR spectroscopy.

EXAMPLE 9

Using the experimental arrangement of Example 1, 97 g (~ quantity including catalyst) of the product $C_4F_9SO_2N(CH_3)CH_2$—$CH(OH)C_2H_5$ were obtained within 3 hours by the reaction of 78.3 g (0.25 mol) of N-methyl-perfluorobutane sulphonamide, 0.3 g (0.0075 mol) of sodium hydroxide and 19 g (0.26 mol) of ethyl oxirane at about 120° C. The product was identified by NMR spectroscopy and gas chromatography.

EXAMPLE 10

108.8 g (~ quantity including catalyst) of the compound $C_4F_9SO_2N(CH_3)CH_2$—$CH(CH)$—$CH_2O$—$CH_2$—$CH$=$CH_2$ were obtained analogously from 78.3 g (0.25 mol) of N-methyl-perfluoro butane sulphoamide, 0.5 g (0.0089 mol) of potassium hydroxide and 30.7 g (0.66 mol) of [(2-propyleneoxy)methyl]oxirane by a reaction at about 110° C. within 3 hours. The product was identified by NMR spectroscopy and gas chromatography.

EXAMPLE 11

117 g (~ quantity including catalyst) of the compound $C_4F_9SO_2N(CH_3)CH_2$—$CH(OH)$—$CH_2$—$O$—$C_6H_5$ melting in the range of from 62° to 65° C. were similarly obtained from 78.3 (0.25 mol) of N-methyl-perfluorobutane sulphonamide, 0.5 g (0.0089 mol) of potassium hydroxide and 39.3 g (0.26 mol) of phenoxymethyloxirane within 3 hours by a reaction at from 120° to 130° C. The product was identified by NMR spectroscopy and gas chromatography.

EXAMPLE 12

38.7 g (~ quantity including catalyst) of the compound $C_4F_9SO_2N(CH_3)CH_2$—$CH(OH)$—$CH_2OH$ melting at about 95° C. were similarly obtained within 3 hours at about 120° C. from 31.3 g (0.1 mol) of N-methyl-perfluorobutane sulphonamide, 0.1 g (0.0018 mol) of potassium hydroxide and 7.4 g (0.1 mol) of glycidol. The product was identified NMR spectroscopy and gas chromatography.

EXAMPLE 13

46 g (~ quantity including catalyst) of the compound $C_4F_9SO_2N(CH_3)CH_2$—$CH(OH)$—$CH_2$—$O$—$CH_2$—$CH(OH)$—$CH_2$—$OH$ melting at about 69° C. were similarly obtained from 31.3 g (0.1 mol) of N-methyl-perfluorobutane sulphonamide, 0.1 g (0.0025 mol) of sodium hydroxide and 14.8 g (0.2 mol) of glycidol within 4 hours at from 120° to 130° C. The product was identified by NMR spectroscopy and gas chromatography.

EXAMPLE 14

44 g (1 mol) of ethylene oxide were added dropwise within 7 hours to 47 g (0.15 mol) of N-methyl-perfluorobutane sulphonamide and 0.5 g (0.0089 mol) of potassium hydroxide by a method similar to that of Example 1 at from 100° to 120° C. After removal of excess ethylene oxide under vacuum, 87 g of a readily water-soluble liquid having an average composition corresponding to the formula $C_4F_9SO_2N(CH_3)(CH_2$—$CH_2$—$O)_6H$ were obtained.

EXAMPLE 15

626 g (2 mol) of N-methyl-perfluorobutane sulphonamide and 5 g (0.089 mol) of potassium hydroxide were introduced into an autoclave and the mixture was melted at about 90° C. The apparatus was put under a nitrogen pressure of about 5 bar. 122 g (2.1 mol) of propylene oxide were introduced, using a Lewa pump. The pressure in the apparatus was released after about 1.5 hours, excess propylene oxide was removed under vacuum and the solvent-free reaction mixture was suction filtered. The compound was obtained analogously to Example 5 and identified by NMR spectroscopy and gas chromatography.

EXAMPLE 16

27.7 g (0.054 mol) of N-methyl-perfluorooctane sulphonamide, 0.2 g (0.005 mol) of sodium hydroxide and 66 g (1.5 mol) of ethylene oxide were introduced into a small autoclave. The mixture was heated to from 120° to 130° C. with stirring and a pressure of about 10 bar became established.

When the pressure was found to be only about 2 bar, the pressure of the apparatus was released through a cooling trap and the apparatus was then degasified under vacuum. 78 g of a waxy, readily water-soluble substance having an average composition corresponding to the formula: $C_8F_{17}SO_2N(CH_3)(CH_2-CH_2-O)_{\sim 22}H$ were obtained.

EXAMPLE 17

Using an experimental arrangement similar to that of Example 1, 357 g ($\sim$ quantity including catalyst) of the compound $C_4F_9SO_2N(CH_3)CH_2CH_2OH$ melting at from 61° to 63° C. were obtained from 313 g (1 mol) of N-methyl-perfluorobutane sulphonamide, 0.6 g (0.015 mol) of sodium hydroxide and 48.5 g (1.1 mol) of ethylene oxide within 3 hours at from 80° to 90° C. The product was identified by NMR spectroscopy and gas chromatography.

EXAMPLE 18

Using the experimental arrangement of Example 1, 88 g ($\sim$ quantity including catalyst) of the compound $C_4F_9SO_2N(C_6H_{11})CH_2-CH(CH_3)OH$ obtained from 76.3 g (0.2 mol) of N-cyclohexyl-perfluorobutane sulphonamide, 0.96 g (0.009 mol) of lithium diisopropylamide and 12.8 g (0.22 mol) of propylene oxide.

EXAMPLE 19

Using the experimental arrangement of Example 1, 87 g ($\sim$ quantity including catalyst) of the compound $C_4F_9SO_2N(CH_2-C_6H_5)CH_2-CH_2-OH$ were obtained from 77.9 g (0.2 mol) of N-benzyl-perfluorobutane sulphonamide, 0.01 mol (dissolved in hexane) of butyl lithium and 10 g (0.23 mol) of ethylene oxide.

EXAMPLE 20

96 g ($\sim$ quantity including catalyst) of the compound $C_4F_9SO_2N(CH_3)CH_2CH(CH_3)OH$ were similarly obtained from 78.3 g (0.25 mol) of N-methyl-perfluorobutane sulphonamide, 3 g (0.0085 mol) of the potassium salt of the sulphamide and 15.25 g (0.26 mol) of propylene oxide.

EXAMPLE 21

The compound of Example 1 was prepared by a method similar to that of Example 1 from 25.7 g (0.05 mol) of N-methyl-perfluorooctane sulphonamide, 0.2 g (0.0036 mol) of potassium hydroxide and 2.5 g (0.056 mol) of ethylene oxide. 3.7 g (0.05 mol) of glycidol were subsequently added at about 120° C. 32 g ($\sim$ quantity) of the compound:

$C_8F_{17}SO_2N(CH_3)CH_2-CH_2-O-CH_2-CH(OH)-CH_2-OH$, which was identified by NMR spectroscopy and gas chromatography, were obtained.

It will be appreciated that the instant specification and examples are set forth by way of illustration and not limitation, and that various modifications and changes may be made without departing from the spirit and scope of the present invention.

What is claimed is:

1. A process for the preparation of a hydroxy-alkyl-perfluoroalkane sulphonamide of the formula

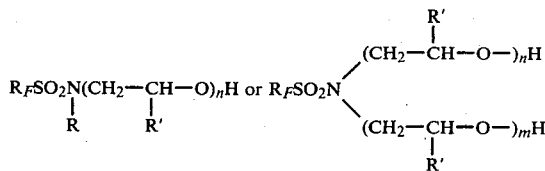

wherein
$R_F$ is a perfluoroalkyl group having from 1 to 20 carbon atoms;
R and R' each independently is hydrogen or an alkyl, hydroxyalkyl, haloalkyl, cycloalkyl, aralkyl, alkenyl or aryl radical; and
m and n each independently is an integer from 1 to about 30, comprising reacting a perfluoroalkylsulphonamide of the formula

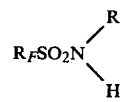

with an epoxide of the formula

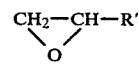

in the presence of a basic catalyst and in the absence of a solvent.

2. A process according to claim 1, wherein the catalyst is potassium hydroxide and/or sodium hydroxide.

3. A process according to claim 1, including the step of washing the reaction product with water, thereby to remove impurities.

4. A process according to claim 1, wherein the basic catalyst is a member selected from the group consisting of alkali or alkaline earth metal oxides, hydroxides and hydrides, alkali metal carbonates and phosphates, metal alkyls, metal aryls, secondary metal amides, metal alcoholates, metal carboxylates, alkali metal salts of the perfluoroalkylsulphonamide, and a basic ion exchange resin.

* * * * *